United States Patent [19]

Laurent et al.

[11] 4,296,109

[45] Oct. 20, 1981

[54] CORTICOID 21-SULFOPROPIONATES AND THE SALTS THEREOF, A PROCESS FOR THE PRODUCTION THEREOF AND PHARMACEUTICAL PREPARATIONS THEREOF

[75] Inventors: Henry Laurent; Peter Esperling; Joachim-Friedrich Kapp; Rudolf Wiechert, all of Berlin, Fed. Rep. of Germany

[73] Assignee: Schering, Aktiengesellschaft, Berlin and Bergkamen, Fed. Rep. of Germany

[21] Appl. No.: 81,947

[22] Filed: Oct. 9, 1979

[30] Foreign Application Priority Data

Oct. 4, 1978 [DE] Fed. Rep. of Germany ....... 2843690
Aug. 6, 1979 [DE] Fed. Rep. of Germany ....... 2032166

[51] Int. Cl.$^3$ ............................................. A61K 31/56
[52] U.S. Cl. ............................... 424/241; 260/397.45; 260/397.4; 260/239.55 D; 424/243
[58] Field of Search ...... 260/397.45, 397.4, 239.55 D; 424/241, 243

[56] References Cited

FOREIGN PATENT DOCUMENTS 2703543  7/1978  Fed. Rep. of Germany ....................... 260/397.47

*Primary Examiner*—Elbert L. Roberts
*Attorney, Agent, or Firm*—Millen & White

[57] ABSTRACT

Corticoid 21-sulfopropionates of the formula

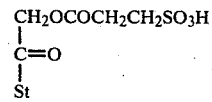

wherein
St is a steroid nucleus of a corticoid having anti-inflammatory activity,
and the salts thereof with physiologically acceptable bases, simultaneously form stable, sterilizable and storable solutions and also are very rapidly cleaved after i.v. administration, yielding the free corticoids as the cleavage product.

28 Claims, No Drawings

CORTICOID 21-SULFOPROPIONATES AND THE SALTS THEREOF, A PROCESS FOR THE PRODUCTION THEREOF AND PHARMACEUTICAL PREPARATIONS THEREOF

BACKGROUND OF THE INVENTION

The present invention relates to corticoid 21-derivatives.

Water-soluble derivatives of corticoids are known and have been utilized for a long time in therapy. Such derivatives include, for example, sodium salts of corticoid 21-hemisulfates, corticoid 21-phosphates, corticoid 21-sulfobenzoates, corticoid 21-hemisuccinates and corticoid 21-aminoacylates.

The sodium salts of corticoid 21-hemisulfates, corticoid 21-phosphates and corticoid 21-sulfobenzoates normally form stable, sterilizable and storable solutions. However, they have the disadvantage that, after i.v. administration, they are split only relatively gradually and in most cases even only incompletely into the free corticoids which are the actual active agents. This disadvantage has an especially grave effect in the treatment of life-endagering shock conditions with such preparations.

The sodium salts of corticoid 21-hemisuccinates and corticoid 21-aminoacylates, on the other hand, are very rapidly cleaved after i.v. administration, so that the actual active corticoids can immediately deploy their full efficacy. The solutions of these compounds, however, are so instable that they cannot be sterilized at high temperature or stored at room temperature. For this reason, the preparations containing them are always dry powders which must be dissolved shortly before application. This is a serious disadvantage since the danger is rather high than the thus-prepared injection solutions will not be sterile, and that a portion of the active ingredient will remain undissolved.

SUMMARY OF THE INVENTION

Accordingly, it is an object of the present invention to provide corticoid derivatives which simultaneously form stable, sterilizable and storable solutions and also are very rapidly cleaved after i.v. administration yielding the free corticoids as the cleavage product.

Upon further study of the specification and appended claims, further objects and advantages of this invention will become apparent to those skilled in the art.

These objects have been attained by providing corticoid 21-sulfopropionates of formula I

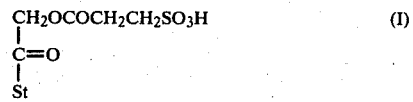

wherein
St is a steroid nucleus of a corticoid having anti-inflammatory activity,
and the salts thereof with physiologically acceptable bases.

Included among these corticoid 21-sulfopropionates of formula I are, in particular, those of Formula II

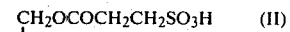

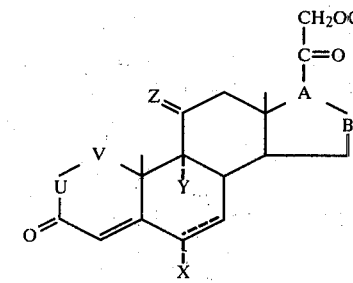

wherein
••• represents a single or double bond;
X is hydrogen, chlorine, fluorine or methyl;
Y is hydrogen, fluorine or chlorine;
Z is oxo, or hydrogen in the α-position and hydroxy in the β-position;
—U—V— represents —CH$_2$—CH$_2$, —CH=CH— or

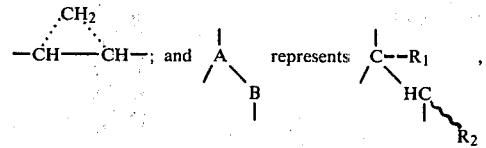

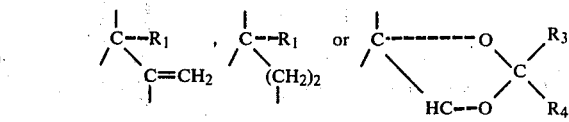

wherein R$_1$ is hydrogen, hydroxy or acyloxy; R$_2$ is hydrogen or methyl; and R$_3$ and R$_4$ are independently each alkyl of 1-4 carbon atoms; and the salts thereof with physiologically acceptable bases;
wherein
............is a double bond;
X is fluorine;
Y is hydrogen, fluorine or chlorine;
Z is hydrogen in the α-position and hydroxy in the β-position; and

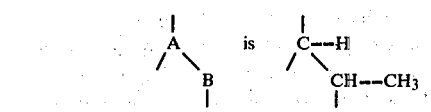

and the salts thereof with physiologically acceptable bases;
wherein
............is a double bond;
X is hydrogen;
Y is fluorine or chlorine;
Z is hydrogen in the α-position and hydroxy in the β-position; and

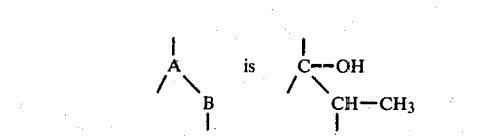

and the salts thereof with physiologically acceptable bases;

wherein

---- is a double bond;
X is hydrogen or fluorine;
Y is hydrogen or fluorine;
Z is hydrogen in the α-position and hydroxy in the β-position; and

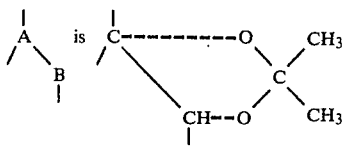

and the salts thereof with physiologically acceptable bases;
wherein
X is hydrogen or methyl;
Y is hydrogen
Z is hydrogen in the α-position and hydroxy in the β-position; and

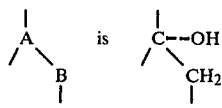

and the salts thereof with physiologically acceptable bases;
and wherein

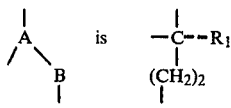

DETAILED DISCUSSION

Suitable acyloxy groups $R_1$ of the corticoid 21-sulfopropionates of Formula II include, preferably, those derived from $C_{1-8}$ hydrocarbon carboxylic acids, e.g., from saturated, straight-chain or branched, aliphatic carboxylic acids (e.g., formic acid, acetic acid, propionic acid, butyric acid, isobutyric acid, pivalic acid, valeric acid or caproic acid) or from benzoic acid.

Suitable alkyl groups for $R_3$ and $R_4$ include methyl, ethyl, propyl, isopropyl, butyl, isobutyl, tert-butyl, etc.

The novel corticoid 21-sulfopropionates can be prepared in a simple way by reacting the corresponding 21-hydroxy steroids in an aprotic solvent with an excess of 3-sulfopropionic anhydride of Formula III

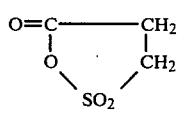

(III)

Suitable solvents include, for example, hydrocarbons, such as benzene or toluene; halogenated hydrocarbons, such as methylene chloride, chloroform, carbon tetrachloride, ethylene chloride, or tetrachloroethane; ethers such as diisopropyl ether, tetrahydrofuran, dioxane or dimethoxyethane; or ketones, such as acetone or methyl isobutyl ketone.

The reaction is preferably conducted at a reaction temperature of 0°–30° C. During the reaction 1.1–10 moles of 3-sulfopropionic anhydride is preferably utilized per mole of corticoid.

The thus-obtained corticoid 21-sulfopropionates can optionally be converted into the salts thereof by reaction with physiologically acceptable bases. Suitable salts include, for example, alkali metal salts (preferably lithium, sodium, or potassium salts), alkaline earth metal salts (preferably magnesium or calcium salts), or salts of amines. Suitable amines include, for example, aliphatic, cycloaliphatic or araliphatic amines each of up to 8 carbon atoms, e.g., 1–8 carbon atoms, and heterocyclic amines (e.g., saturated N-containing heterocycles of 4–7 ring atoms also containing one additional heteroatom of O, N or S), as well as substituted equivalents thereof, e.g., mono-, di- and triethylamine, mono-, di- and trimethylamine, mono-, di- and triisopropylamine, ethyldimethylamine, benzyldiethylamine, cyclohexylamine, dibenzylamine, N,N-dibenzylethyldiamine, bis(o-methoxyphenyl)isopropylamine, methoxyphenylisopropylamine, piperidine, morpholine, pyrrolidine, piperazine, and lower $C_{1-4}$ alkyl derivatives thereof, such as 1-methylpiperidine, 4-ethylmorpholine, 1-isopropylpyrrolidine, 1,4-dimethylpiperazine, 1-n-butylpiperidine, 2-methylpiperidine, 1-methyl-2-methylpiperidine; furthermore, amines with water-soluble or hydrophilic groups, such as mono-, di-, and triethanolamine, ethyldiethanolamine, N-butylmonoethanolamine, 2-amino-1-butanol, 2-amino-2-ethyl-1,3-propanediol, 2-amino-2-methyl-1-propanol, phenylmonoethanolamine, p-tertamylphenyldiethanolamine, galactamine, N-methylglucamine, N-methylglucosamine, ephedrine, phenylephrine, epinephrine, procaine, 2-(4'-tert-butyl-2',6'-dimethylphenylmethyl)imidazoline and the like.

The novel corticoid 21-sulfopropionates of this invention and especially the salts thereof with physiologically acceptable bases are distinguished over the corresponding free 21-hydroxycorticoids in that they are compounds readily soluble in water. In addition, they are distinguished over the known water-soluble derivatives of the same corticoids in that their aqueous solutions are so stable that they can be heat-sterilized and stored and simultaneously additionally are very rapidly split after i.v. administration, as can be seen from the results of the endotoxic shock test set forth below.

For the endotoxin shock test, respectively 10 rats weighing 100–120 g were adrenalectomized and then received, on the following day, under slight ether narcosis 5 μg of endotoxin per 100 g of body weight by intravenous injection. Directly after this injection, the corticoid solution was applied via the same cannula. The number of animals which survived 24 hours after this treatment was determined.

| | RESULTS OF THE ENDOTOXIN SHOCK TEST | | |
|---|---|---|---|
| No. | Compound | Dose in mg./kg. Animal | Number of Surviving Animals |
| | (A) Derivatives of dexamethasone (= 9α-fluoro-11β,17α,-21-trihydroxy-16α-methyl-1,4-pregnadiene-3,20-dione) | | |
| 1 | Sodium dexamethasone | 0.03 | 0 |

-continued

RESULTS OF THE ENDOTOXIN SHOCK TEST

| No. | Compound | Dose in mg./kg. Animal | Number of Surviving Animals |
|---|---|---|---|
|  | 21-hemisulfate | 0.3 | 1 |
| 2 | Sodium dexamethasone 21-o-sulfobenzoate | 0.03<br>0.3 | 2<br>8 |
| 3 | Sodium dexamethasone 21-(3-sulfopropionate) | 0.03<br>0.3 | 10<br>10 |
|  | (B) Derivatives of methylprednisolone |  |  |
|  | (= 11α,17β,21-trihydroxy-6α-methyl-1,4-pregnadiene-3,20-dione) |  |  |
| 4 | Sodium methylprednisolone 21-hemisuccinate | 0.1<br>1.0 | 3<br>9 |
| 5 | Sodium methylprednisolone 21-m-sulfobenzoate | 0.1<br>1.0 | 0<br>4 |
| 6 | Sodium methylprednisolone 21-(3-sulfopropionate) | 0.1<br>1.0 | 5<br>9 |
|  | (C) Derivatives of diflucortolone |  |  |
|  | (= 6α,9α-difluoro-11β,-21-dihydroxy-16α-methyl-1,4-pregnadiene-3,20-dione) |  |  |
| 7 | Sodium diflucortolone 21-hemisulfate | 0.003<br>0.03 | 0<br>0 |
| 8 | Sodium diflucortolone 21-(3-sulfopropionate) | 0.03<br>0.3 | 0<br>10 |
| 9 | Potassium diflucortolone 21-(3-sulfopropionate) | 0.03<br>0.3 | 0<br>10 |
|  | (D) Derivatives of triamcinolone acetonide |  |  |
|  | (= 9 α-fluoro-11α,21-dihydroxy-16α,17α-isopropylidenedioxy)-1,4-pregnadiene-3,20-dione) |  |  |
| 10 | Sodium triamcinoline acetonide 21-phosphate | 0.03<br>0.3 | 0<br>7 |
| 11 | Sodium triamcinoline acetonide 21-hemisuccinate | 0.03<br>0.3 | 6<br>9 |
| 12 | Sodium triamcinolone acetone 21-(3-sulfopropionate) | 0.03<br>0.03 | 6<br>10 |

It is to be noted that the water solubility, especially of the alkali metal salts, of the novel corticoid 21-sulfopropionates is often astonishingly high. Thus, for example, the following quantities can be dissolved in one milliliter of water at 25° C.:

about 350 mg of sodium prednisolone 21-(3-sulfopropionate);

about 350 mg of sodium 6α-methylprednisolone 21-(3-sulfopropionate);

about 500 mg of sodium betamethasone 2-(3-sulfopropionate); and about 350 mg of sodium diflucortolone 21-(3-sulfopropionate).

Accordingly, these compounds are very well suited for the preparation of high-dosage, aqueous injection solutions required for the treatment of life-endagering shock conditions in patients including humans.

In contrast thereto, the water solubility of the sodium salts of corticoid 21-sulfobenzoates is substantially lower. Thus, for example, only the following quantities can be dissolved in one milliliter of water at 25° C.:

about 10 mg of sodium prednisolone 21-(m-sulfobenzoate); and about 3.5 mg of sodium dexamethasone 21-(m-sulfobenzoate).

The compatibility of the novel compounds depends essentially on the compatibility of the 21-hydroxycorticoid systemically liberated therefrom. The 3-sulfopropionic acid released during the cleavage does not cause any side effects in the dosage range utilized.

The novel corticoid 21-sulfopropionates and the salts thereof can be made into drug specialties in a fully conventional manner, e.g., by converting them, optionally with suitable additives, vehicles and stabilizers, into the desired forms of application, such as injection solutions, eye drops, nose drops, enemas, lozenges, tablets or inhalation solutions.

The compounds of Formula I can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the compounds of this invention. Suitable pharmaceutically acceptable carriers include but are not limited to water, salt solutions, alcohols, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The thus-obtained medicinal specialties can serve for the treatment of diseases wherein corticoid therapy is customarily indicated. These include, for example: grave allergic diseases, allergic shock, acute life-endagering conditions, shock, collapse, asthmatic conditions, cerebral edema, transfusion incidents, acute poisoning, extensive burns, Quincke's edema, grave metabolic disturbances, acute grave dermatoses, acute infectious diseases (supplementary therapy), pseudocroup (in children), newly incurred cardiac infarction, lung edema due to inhalation of toxic substances, acute adrenal gland insufficiency, hyperthyroid crisis, Waterhouse-Friderichsen syndrome, apoplexia, Intra-articular: rheumatoid polyarthritis, acute and chronic diseases of the connective tissue, arthrosis deformans, allergic, rheumatologic, and dermatologic diseases responding to oral corticoid therapy, corticoid-sensitive inflammations of the oral mucous membrane, allergic reactions, lichen, pemphigoids, inflammatory and allergic diseases of the eye, iritis, iridocyclitis, conjunctivitis, blepharitis, diseases of the anterior uvea, allergic and chronic rhinitides, rhinitis vasomotorica, non-purulent sinusitis, hay fever and colitis ulcerosa.

Without further elaboration, it is believed that one skilled in the art can, using the preceding description, utilize the present invention to its fullest extent. The folowing preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(A) A solution of 4.5 g. of 3-sulfopropionic anhydride in 150 ml. of methylene chloride is combined with 4.5 g. of 6α-fluoro-11α,21-dihydroxy-16α-methyl-1,4-pregnadiene-3,20-dione and stirred in an ice bath for 2 hours. During this time, a precipitate is formed which, after removing the methylene chloride phase by decanting, is dissolved in 100 ml. of water. The aqueous solution is extracted in succession with respectively 100 ml. of a mixture of methylene chloride and isopropyl alcohol in ratios of (9:1), (8:2), (7:3), and (6:4). The extract obtained with mixture (7:3) yields, after vacuum evaporation, 4.2 g. of 6α-fluoro-11α-hydroxy-16α-methyl-21-(3-sulfopropionyloxy)-1,4-pregnadiene-3,20-dione.

(B) 513 mg. of 6α-fluoro-11α-hydroxy-16α-methyl-21-(3-sulfopropionyloxy)-1,4-pregnadiene-3,20-dione is dissolved in 10 ml. of distilled water and, while controlling the pH, with the use of a glass electrode, titrated with aqueous 0.1 N sodium hydroxide solution to a pH of 7.0. The salt solution is extracted three times with respectively 50 ml. of diethyl ether and then freeze-dried under vacuum at 0.1 mbar. Yield: 496 mg. of the sodium salt of 6α-fluoro-11α-hydroxy-16α-methyl-21-(3-sulfopropionyloxy)-1,4-pregnadiene-3,20-dione in the form of a loose white powder, m.p. 190°–200° C. $[\alpha]_D^{25} = +94°$ (methanol). UV: $\epsilon_{242} = 15,700$ (methanol).

EXAMPLE 2

802 mg. of 6α-fluoro-11β-hydroxy-16α-methyl-21-(3-sulfopropionyloxy)-1,4-pregnadiene-3,20-dione in aqueous 0.1 N potassium hydroxide solution is converted into the potassium salt under the conditions indicated in Example 1(B). Yield: 698 mg., m.p. 190°–200° C. $[\alpha]_D^{25} = +94°$ (water). UV: $\epsilon_{242} = 14,200$ (methanol).

EXAMPLE 3

Under the conditions indicated in Example 1(B), 461 mg. of 6α-fluoro-11β-hydroxy-16α-methyl-21-(3-sulfopropionyloxy)-1,4-pregnadiene-3,20-dione in aqueous 0.1 N lithium hydroxide solution is converted into the lithium salt. Yield: 370 mg., m.p. 200°–210° C. $[\alpha]_D^{25} = +99°$ (water). UV: $\epsilon_{243} = 13,500$ (methanol).

EXAMPLE 4

513 mg. of 6α-fluoro-11β-hydroxy-16α-methyl-21-(3-sulfopropionyloxy)-1,4-pregnadiene-3,20-dione is converted with aqueous 0.1 N ammonium hydroxide solution into the ammonium salt under the conditions described in Example 1(B). Yield: 440 mg., m.p. 169°–176° C. $[\alpha]_D^{25} = +100°$ (water). UV: $\epsilon_{242} = 14,900$ (methanol).

EXAMPLE 5

(A) 4.5 g. of 6α,9α-difluoro-11α,21-dihydroxy-16α-methyl-1,4-pregnadiene-3,20-dione is converted, under the conditions set forth in Example 1(A), into 6α,9α-difluoro-11β-hydroxy-16α-methyl-21-(3-sulfopropionyloxy)-1,4-pregnadiene-3,20-dione. Yield: 3.32 g. (triturated with diethyl ether), m.p. 222°–227° C. (under decomposition).

(B) Under the conditions described in Example 1(B), 1.06 g. of 6α,9α-difluoro-11β-hydroxy-16α-methyl-21-(3-sulfopropionyloxy)-1,4-pregnadiene-3,20-dione is converted into the sodium salt. Yield: 870 mg., m.p. 200°–225° C. $[\alpha]_D^{25} = +94°$ (methanol). UV: $\epsilon_{238} = 16,000$ (methanol).

EXAMPLE 6

796 mg. of 6α,9α-difluoro-11β-hydroxy-16α-methyl-21-(3-sulfopropionyloxy)-1,4-pregnadiene-3,20-dione is converted, under the conditions of Example 1(B), into the potassium salt with aqueous 0.1 N potassium hydroxide solution. Yield: 800 mg., m.p. 207°–215° C. $[\alpha]_D^{25} = +98°$ (water). UV: $\epsilon_{238} = 15,900$ (methanol).

EXAMPLE 7

530 mg. of 6α,9α-difluoro-11β-hydroxy-16α-methyl-21-(3-sulfopropionyloxy)-1,4-pregnadiene-3,20-dione is converted, under the conditions set forth in Example 1(B), into the lithium salt with aqueous 0.1 N lithium hydroxide solution. Yield: 498 mg., m.p. 210°–220° C. $[\alpha]_D^{25} = +98°$ (water). UV: $\epsilon_{238} = 15,400$ (methanol).

EXAMPLE 8

Under the conditions indicated in Example 1(B), 638 mg. of 6α,9α-difluoro-11β-hydroxy-16α-methyl-21-(3-sulfopropionyloxy)-1,4-pregnadiene-3,20-dione is converted into the ammonium salt with aqueous 1 N ammonium hydroxide solution. Yield: 578 mg., m.p. 168°–184° C. $[\alpha]_D^{25} = +104°$ (water). UV: $\epsilon_{238} = 16,000$ (methanol).

EXAMPLE 9

531 mg. of 6α,9α-difluoro-11β-hydroxy-16α-methyl-21-(3-sulfopropionyloxy)-1,4-pregnadiene-3,20-dione is converted into the calcium salt with aqueous 0.04 N calcium hydroxide solution under the conditions indicated in Example 1(B). Yield: 456 mg. $[\alpha]_D^{25} = +93°$ (water). UV: $\epsilon_{238} = 28,200$ (methanol).

EXAMPLE 10

(A) 4.5 g. of 11β,17,21-trihydroxy-1,4-pregnadiene-3,20-dione is converted into 11β,17-dihydroxy-21-(3-sulfopropionyloxy)-1,4-pregnadiene-3,20-dione under the conditions set forth in Example 1(A). Yield: 2.28 g.

(B) 680 mg. of 11β,17-dihydroxy-21-(3-sulfopropionyloxy)-1,4-pregnadiene-3,20-dione is converted into the sodium salt under the conditions set forth in Example 1(B). Yield: 500 mg., m.p. 180°–200° C. (under decomposition). $[\alpha]_D^{25} = +79°$ (methanol). UV: $\epsilon_{243} = 10,600$ (methanol).

EXAMPLE 11

(A) Under the conditions described in Example 1(A), 1.0 g. of 11β,17,21-trihydroxy-6α-methyl-1,4-pregnadiene-3,20-dione is converted into 11β,17-dihydroxy-6α-methyl-21-(3-sulfopropionyloxy)-1,4-pregnadiene-3,20-dione. Yield: 600 mg.

(B) 580 mg. of 11β,17-dihydroxy-6α-methyl-21-(3-sulfopropionyloxy)-1,4-pregnadiene-3,20-dione is converted into the sodium salt under the conditions set forth in Example 1(B). Yield: 470 mg., m.p. 206°–224° C. $[\alpha]_D^{25} = +87°$ (water). UV: $\epsilon_{243} = 13,100$ (methanol).

EXAMPLE 12

(A) Under the conditions described in Example 1(A), 3.0 g. of 9α-fluoro-11β,21-dihydroxy-16α,17-isopropylidenedioxy-1,4-pregnadiene-3,20-dione is converted into 9α-fluoro-11α-hydroxy-16α,17-isopropylidenedioxy-21-(3-sulfopropionyloxy)-1,4-pregnadiene-3,20-dione. Yield: 2.1 g.

(B) 742 mg. of 9α-fluoro-11β-hydroxy-16α,17-isopropylidenedioxy-21-(3-sulfopropionyloxy)-1,4-pregnadiene-3,20-dione is converted into the sodium salt under the conditions described in Example 1(B). Yield: 704 mg., m.p. 238°–243° C. $[\alpha]_D^{25} = +93°$ (water). UV: $\epsilon_{238} = 14,100$ (methanol).

EXAMPLE 13

(A) Under the conditions set forth in Example 1(A), 2.5 g. of 9α-fluoro-11β,17,21-trihydroxy-16α-methyl-1,4-pregnadiene-3,20-dione is converted into 9α-fluoro-11β,17-dihydroxy-16α-methyl-21-(3-sulfopropionyloxy)-1,4-pregnadiene-3,20-dione. Yield: 992 mg.

(B) 950 mg. of 9α-fluoro-11β,17-dihydroxy-16α-methyl-21-(3-sulfopropionyloxy)-1,4-pregnadiene-3,20-dione is converted into the sodium salt under the conditions described in Example 1(b). Yield: 690 mg., m.p. 215°–230° C. $[\alpha]_D^{25} = +81°$ (water). UV: $\epsilon_{235} = 14,200$ (methanol).

EXAMPLE 14

(A) 2.5 g of 9α-chloro-6α-fluoro-11β,21-dihydroxy-16α-methyl-1,4-pregnadiene-3,20-dione is converted, under the conditions indicated in Example 1(A, into 9α-chloro-6α-fluoro-11β-hydroxy-16α-methyl-21-(3-sulfopropionyloxy)-1,4-pregnadiene-3,20-dione. Yield: 1.96 g. (after trituration with diethyl ether).

(B) 547 mg. of 9α-chloro-6α-fluoro-11β-hydroxy-16α-methyl-21-(3-sulfopropionyloxy)-1,4-pregnadiene-3,20-dione is converted into the sodium salt under the conditions set forth in Example 1(B). Yield: 508 mg., m.p. 201°–230° C. (under decomposition). $[\alpha]_D^{25} = +122°$ (water). UV: $\epsilon_{237} = 15,000$ (methanol).

EXAMPLE 15

(A) 1.1 g. of 9α-fluoro-11β,21-dihydroxy-16α-methyl-1,4-pregnadiene-3,20-dione is converted into 9α-fluoro-11β-hydroxy-16α-methyl-21-(3-sulfopropionyloxy)-1,4-pregnadiene-3,20-dione under the conditions described in Example 1(A). Yield: 460 mg.

(B) 460 mg. of 9α-fluoro-11β-hydroxy-16α-methyl-21-(3-sulfopropionyloxy)-1,4-pregnadiene-3,20-dione is converted into the sodium salt under the conditions indicated in Example 1(B). Yield: 427 mg., m.p. 189°–200° C. $[\alpha]_D^{25} = +103°$ (water). UV: $\epsilon_{239} = 14,300$ (methanol).

EXAMPLE 16

(A) 2.0 g. of 9α-fluoro-11β,17,21-trihydroxy-16β-methyl-1,4-pregnadiene-3,20-dione is converted, under the conditions described in Example 1(A), into 9α-fluoro-11β,17-dihydroxy-16β-methyl-21-(3-sulfopropionyloxy)-1,4-pregnadiene-3,20-dione. Yield: 970 mg.

(B) 970 mg. of 9α-fluoro-11β,17-dihydroxy-16β-methyl-21-(3-sulfopropionyloxy)-1,4-pregnadiene-3,20-dione is converted into the sodium salt under the conditions set forth in Example 1(B). Yield: 742 mg., m.p. 205°–220° C. $[\alpha]_D^{25} = +82°$ (water). UV: $\epsilon_{238} = 13,200$ (methanol).

EXAMPLE 17

(A) Under the conditions set forth in Example 1(A), 2.0 g. of 11β,17,21-trihydroxy-4-pregnene-3,20-dione is converted into 11β,17-dihydroxy-21-(3-sulfopropionyloxy)-4-pregnene-3,20-dione. Yield: 520 mg.

(B) 520 mg. of 11β,17-dihydroxy-21-(3-sulfopropionyloxy)-4-pregnene-3,20-dione is converted into the sodium salt under the conditions indicated in Example 1(B). Yield: 382 mg., m.p. 192°–210° C. $[\alpha]_D^{25} = +123°$ (water). UV: $\epsilon_{243} = 14,400$ (methanol).

EXAMPLE 18

(A) Under the conditions indicated in Example 1(A), 1.0 g. of 9α-fluoro-11β,17,21-trihydroxy-4-pregnene-3,20-dione is converted into 9α-fluoro-11β,17-dihydroxy-21-(3-sulfopropionyloxy)-4-pregnene-3,20-dione. Yield: 900 mg.

(B) Under the conditions described in Example 1(B), 900 mg. of 9α-fluoro-11β,17-dihydroxy-21-(3-sulfopropionyloxy)-4-pregnene-3,20-dione is converted into the sodium salt. Yield: 610 mg., m.p. 205°–225° C. $[\alpha]_D^{25} = +109°$ (water). UV: $\epsilon_{239} = 14,300$ (methanol).

EXAMPLE 19

(A) 2.5 g. of 9α-fluoro-11β,21-dihydroxy-16β-methyl-17-valeryloxy-1,4-pregnadiene-3,20-dione is converted into 9α-fluoro-11β-hydroxy-16β-methyl-21-(3-sulfopropionyloxy)-17-valeryloxy-1,4-pregnadiene-3,20-dione under the conditions described in Example 1(A). Yield: 2.37 g.

(B) 890 mg. of 9α-fluoro-11β-hydroxy-16β-methyl-21-(3-sulfopropionyloxy)-17-valeryloxy-1,4-pregnadiene-3,20-dione is converted into the sodium salt as indicated in Example 1(B). Yield: 550 mg., m.p. 190°–198° C. $[\alpha]_D^{25} = +81°$ (water). UV: $\epsilon_{239} = 14,600$ (methanol).

EXAMPLE 20

1.4 g. of 9α-fluoro-11β-hydroxy-16β-methyl-21-(3-sulfopropionyloxy)-17-valeryloxy-1,4-pregnadiene-3,20-dione is converted into the potassium salt under the conditions set forth in Example 1(B) with aqueous 0.1 N potassium hydroxide solution. Yield: 960 mg., m.p. 196°–200° C. $[\alpha]_D^{25} = +78°$ (water). UV: $\epsilon_{240} = 14,900$ (methanol).

EXAMPLE 21

(A) 1.9 g. of 17-butyryloxy-11β,21-dihydroxy-4-pregnene-3,20-dione is converted, under the conditions listed in Example 1(A), into 17-butyryloxy-11β-hydroxy-21-(3-sulfopropionyloxy)-4-pregnene-3,20-dione. Yield: 600 mg.

(B) 500 mg. of 17-butyryloxy-11β-hydroxy-21-(3-sulfopropionyloxy)-4-pregnene-3,20-dione is converted into the sodium salt under the conditions indicated in Example 1(B). Yield: 300 mg., m.p. 230°–253° C. (under decomposition). $[\alpha]_D^{25} = +68°$ (water). UV: $\epsilon_{239} = 15,800$ (methanol).

EXAMPLE 22

(A) Under the conditions described in Example 1(A), 1.0 g. of 6α-fluoro-11β,17,21-trihydroxy-1,4-pregnadiene-3,20-dione is converted into 6α-fluoro-11β,17-dihydroxy-21-(3-sulfopropionyloxy)-1,4-pregnadiene-3,20-dione. Yield: 590 mg.

(B) 500 mg. of 6α-fluoro-11β,17-dihydroxy-21-(3-sulfopropionyloxy)-1,4-pregnadiene-3,20-dione is converted into the sodium salt under the conditions described in Example 1(B). Yield: 450 mg., m.p. 230°–278° C. (under decomposition). $[\alpha]_D^{25} = +91°$ (water). UV: $\epsilon_{240} = 13,800$ (methanol).

EXAMPLE 23

(A) Under the conditions set forth in Example 1(A), 490 mg. of 11β,17aα,21-trihydroxy-D-homo-1,4-pregnadiene-3,20-dione is converted into 11β,17aα-dihydroxy-21-(3-sulfopropionyloxy)-D-homo-1,4-pregnadiene-3,20-dione. Yield: 290 mg.

(B) 290 mg. of 11β,17aα-dihydroxy-21-(3-sulfopropionyloxy)-D-homo-1,4-pregnadiene-3,20-dione is converted into the sodium salt under the conditions indicated in Example 1(B). Yield: 250 mg., m.p. 220°–274° C. (under decomposition). $[\alpha]_D^{25} = +92°$ (methanol). UV: $\epsilon_{244} = 10,700$ (methanol).

EXAMPLE 24

(A) Under the conditions set forth in Example 1(A), 495 mg. of 9α-fluoro-11β,17aα,21-trihydroxy-D-homo-1,4-pregnadiene-3,20-dione is converted into 9-fluoro-11β,17aα-dihydroxy-21-(3-sulfopropionyloxy)-D-homo-1,4-pregnadiene-3,20-dione. Yield: 440 mg.

(B) 440 mg. of 9α-fluoro-11β,17aα-dihydroxy-21-(3-sulfopropionyloxy)-D-homo-1,4-pregnadiene-3,20-dione is converted into the sodium salt under the conditions indicated in Example 1(B). Yield: 370 mg., m.p. 235°–283° C. (under decomposition). $[\alpha]_D^{25} = +91°$ (methanol). UV: $\epsilon_{240} = 13,400$ (methanol).

EXAMPLE 25

(A) Under the conditions set forth in Example 1(A), 500 mg. of 6-chloro-11β,17,21-trihydroxy-1,4,6-pregnatriene-3,20-dione is converted into 6-chloro-11β,17-dihydroxy-21-(3-sulfopropionyloxy)-1,4,6-pregnatriene-3,20-dione. Yield: 380 mg.

(B) 380 mg. of 6-chloro-11β,17-dihydroxy-21-(3-sulfopropionyloxy)-1,4,6-pregnatriene-3,20-dione is converted into the sodium salt under the conditions disclosed in Example 1(B). Yield: 350 mg., m.p. 190°–240° C. (under decomposition). $[\alpha]_D^{25} = +48°$ (methanol). UV: $\epsilon_{227} = 9,100$, $\epsilon_{255} = 8,100$, $\epsilon_{298} = 8,000$ (methanol).

EXAMPLE 26

(A) A solution of 10 g. of 6-chloro-17-hydroxy-1α,2α-methylene-4,6-pregnadiene-3,20-dione in 75 ml. of methanol and 75 ml. of tetrahydrofuran is combined with 15 g. of calcium oxide and 500 mg. of azoisobutyronitrile. Several milliliters of a solution of 10 g. of iodine in 50 ml. of tetrahydrofuran and 30 ml. of methanol are added dropwise to the reaction mixture. After an induction time of 60 minutes, the solution loses its color; the residual iodine solution is added dropwise within 8 hours. The reaction mixture is diluted with 500 ml. of dichloromethane, the calcium oxide is filtered off, and the filtrate is washed with sodium thiosulfate solution and water, dried over sodium sulfate, and concentrated under vacuum at 35° C., thus obtaining 13 g. of 6-chloro-17-hydroxy-21-iodo-1α,2α-methylene-4,6-pregnadiene-3,20-dione. This product is dissolved in 130 ml. of acetone and 45 ml. of acetic acid, combined with 69 ml. of triethylamine, and refluxed for 90 minutes. The solution is stirred into ice water. The thus-obtained precipitate is isolated and chromatographed on silica gel. With 16–20% acetone-pentane, 6.1 g. of 21-acetoxy-6-chloro-17-hydroxy-1α,2α-methylene-4,6-pregnadiene-3,20-dione is obtained, m.p. 224° C.

(B) A 2-liter Erlenmeyer flask, containing 500 ml. of a nutrient solution of 1% corn steep liquor, 1% soybean meal, and 0.005% soybean oil sterilized for 30 minutes in an autoclave at 120° C., and adjusted to pH 6.2, is inoculated with a lyophilized culture of *Curvularia lunata* (NRRL 2380) and shaken on a rotary shaker for 72 hours at 30° C. With this subculture, a 20-liter fermentor is then inoculated, this fermentor containing 15 l. of a medium of 1% corn steep liquor, 0.5% glucose, and 0.005% soybean oil, sterilized at 121° C. and 1.1 atmospheres guage and adjusted to pH 6.2. With the addition of silicone SH as a defrothing agent, the culture is germinated at 29° C. under aeration (10 l./min.), under a pressure of 0.7 atm. guage, and under agitation (220 r.p.m.) for 24 hours. One liter of the culture broth is transferred under sterile conditions into 14 l. of a medium, sterilized as above, of 1% corn steep liquor, 1.25% soybean meal, and 0.005% soybean oil and incubated under the same conditions. After 12 hours, a solution of 15 g. of 21-acetoxy-6-chloro-17-hydroxy-1α,2α-methylene-4,6-pregnadiene-3,20-dione in 150 ml. of dimethylformamide is added thereto, and the culture is further agitated and aerated. After 26 hours of contact time, the content of the fermentor is extracted twice with respectively 10 l. of methyl isobutyl ketone, and the combined extracts are evaporated under vacuum at a bath temperature of 50° C. The residue is taken up in methanol, the undissolved silicone oil is separated, the solution is treated with activated carbon, and made to crystallize after concentration. The thus-separated crystalline product is chromatographed for further purification over a silica gel column by means of a methylene chloride-acetone gradient and then recrystallized from acetone-methanol. The pure 6-chloro-11β,17,21-trihydroxy-1α,2α-methylene-4,6-pregnadiene-3,20-dione (8.1 g.) melts at 271°–272° C. $[\alpha]_D^{25} = +273°$ (methanol). UV: $\epsilon_{283} = 17,300$ (methanol).

(C) 1.09 g. of 6-chloro-11β,17,21-trihydroxy-1α,2α-methylene-4,6-pregnadiene-3,20-dione is converted, under the conditions set forth in Example 1(A), into 6-chloro-11β,17-dihydroxy-1α,2α-methylene-21-(3-sulfopropionyloxy)-4,6-pregnadiene-3,20-dione. Yield: 620 mg.

(D) 620 mg. of 6-chloro-11β,17-dihydroxy-1α,2α-methylene-21-(3-sulfopropionyloxy)-4,6-pregnadiene-3,20-dione is converted into the sodium salt under the conditions indicated in Example 1(B). Yield: 260 mg., m.p. 238°–281° C. (under decomposition). $[\alpha]_D^{25} = +194°$ (methanol). UV: $\epsilon_{283} = 14,000$ (methanol).

GALENIC PREPARATIONS

Example I

Eye Drop Composition:
100 mg. of sodium 9α-fluoro-11β,17-dihydroxy-16β-methyl-21-(3-sulfopropionyloxy)-1,4-pregnadiene-3,20-dione
2 mg. of benzalkonium chloride and
700 mg. of sodium chloride
are dissolved in 100 ml. of water for injection purposes. The solution is sterilized and dispensed under aseptic conditions.

Example II

Ear Drop Composition:
0.2 g. of sodium 6α,9α-difluoro-11β-hydroxy-16α-methyl-21-(3-sulfopropionyloxy)-1,4-pregnadiene-3,20-dione
1.5 g. of chloramphenicol
98.3 g. of 1,2-propanediol.

Example III

Nose Drop Composition:
25 mg. of sodium 9α-fluoro-11β,17-dihydroxy-16α-methyl-21-(3-sulfopropionyloxy)-1,4-pregnadiene-3,20-dione and
50 mg. of oxymetazoline hydrochloride
are dissolved in 100 ml. of aqua bidestillata. The solution is sterilized and dispensed under aseptic conditions.

Example IV

Solutions for Intravenous Injection:
(A) 10.0 g. of sodium 11β,17-dihydroxy-6α-methyl-21-(3-sulfopropionyloxy)-1,4-pregnadiene-3,20-dione is dissolved in 100 ml. of water for injection purposes. The solution is filtered clear and dispensed into ampoules. The sealed ampoules are heated for 30 minutes to 115° C. under pressurized steam.

(B) 5.0 g. of potassium 6α-fluoro-11β-hydroxy-16α-methyl-21-(3-sulfopropionyloxy)-1,4-pregnadiene-3,20-dione is dissolved in 100 ml. of water for injection purposes. The solution is dispensed and sterilized as described above.

Example V

Composition of a Tablet for Oral Administration:
5.00 mg. of sodium 11β,17-dihydroxy-21-(3-sulfopropionyloxy)-1,4-pregnadiene-3,20-dione
71.47 mg. of corn starch, DAB 7 [German Pharmacopoeia]
36.00 mg. of lactose, DAB 7
6.00 mg. of talc, DAB 7
1.50 mg. of gelatin, white, DAB 7
0.02 mg. of methyl p-hydroxybenzoate, DAB 7
0.01 mg. of propyl p-hydroxybenzoate, DAB 7.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A corticoid 21-sulfopropionate of the formula

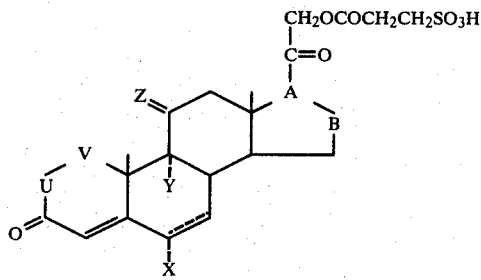

wherein
........... represents a single of double bond;
X is hydrogen, chlorine, fluorine or methyl;
Y is hydrogen, fluorine or chlorine;
Z is oxo, or hydrogen in the α-position and hydroxy in the β-position;
—U—V represents —$CH_2$—$CH_2$—, —CH=CH— or

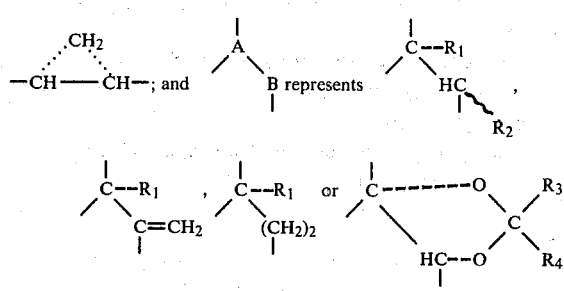

wherein $R_1$ is hydrogen, hydroxy or acyloxy, wherein the acyl group is derived from a $C_{1-8}$ hydrocarbon carboxylic acid; $R_2$ is hydrogen or methyl; and $R_3$ and $R_4$ are independently each alkyl of 1-4 carbon atoms; and the salts thereof with physiologically acceptable bases.

2. A corticoid 21-sulfopropionate of claim 1, wherein
........... is a double bond;
X is fluorine;
Y is hydrogen, fluorine or chlorine;
Z is hydrogen in the α-position and hydroxy in the β-position; and

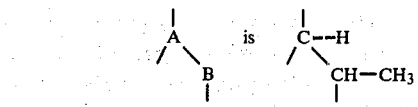

and the salts thereof with physiologically acceptable bases.

3. A corticoid 21-sulfopropionate of claim 1, wherein
........... is a double bond;
X is hydrogen;
Y is fluorine or chlorine;
Z is hydrogen in the α-position and hydroxy in the β-position; and

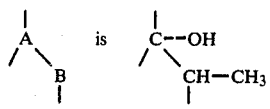

and the salts thereof with physiologically acceptable bases.

4. A corticoid 21-sulfopropionate of claim 1, wherein
........... is a double bond;
X is hydrogen or fluorine;
Y is hydrogen or fluorine;
Z is hydrogen in the α-position and hydroxy in the β-position; and

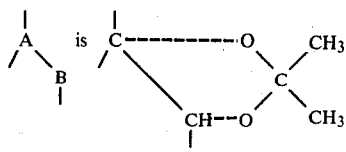

and the salts thereof with physiologically acceptable bases.

5. A corticoid 21-sulfopropionate of claim 1, wherein
X is hydrogen or methyl;
Y is hydrogen;
Z is hydrogen in the α-position and hydroxy in the β-position; and

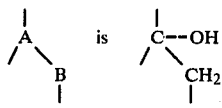

and the salts thereof with physiologically acceptable bases.

6. A corticoid 21-sulfopropionate of claim 1, wherein

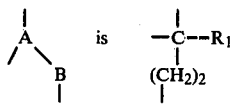

7. A lithium, sodium, potassium, calcium or ammonium salt of a corticoid 21-sulfopropionate of claim 1.

8. 6α-Fluoro-11β-hydroxy-16α-methyl-21-(3-sulfopropionyloxy)-1,4-pregnadiene-3,20-dione and the sodium, potassium, lithium or ammonium salts thereof.

9. 6α,9α-Difluoro-11β-hydroxy-16α-methyl-21-(3-sulfopropionyloxy)-1,4-pregnadiene-3,20-dione and the sodium, potassium, lithium, calcium or ammonium salts thereof.

10. 11β,17α-Dihydroxy-21-(3-sulfopropionyloxy)-1,4-pregnadiene-3,20-dione and the sodium salt thereof.

11. 11β,17α-Dihydroxy-6α-methyl-21-(3-sulfopropionyloxy)-1,4-pregnadiene-3,20-dione and the sodium salt thereof.

12. 9α-Fluoro-11β-hydroxy-16α,17α-isopropylidenedioxy-21-(3-sulfopropionyloxy)-1,4-pregnadiene-3,20-dione and the sodium salt thereof.

13. 9α-Fluoro-11β,17α-dihydroxy-16α-methyl-21-(3-sulfopropionyloxy)-1,4-pregnadiene-3,20-dione and the sodium salt thereof.

14. 9α-Chloro-6α-fluoro-11β-hydroxy-16α-methyl-21-(3-sulfopropionyloxy)-1,4-pregnadiene-3,20-dione and the sodium salt thereof.

15. 9α-Fluoro-11β-hydroxy-16α-methyl-21-(3-sulfopropionyloxy)-1,4-pregnadiene-3,20-dione and the sodium salt thereof.

16. 9α-Fluoro-11β,17α-dihydroxy-16β-methyl-21-(3-sulfopropionyloxy)-1,4-pregnadiene-3,20-dione and the sodium salt thereof.

17. 11β,17α-Dihydroxy-21-(3-sulfopropionyloxy)-4-pregnene-3,20-dione and the sodium salt thereof.

18. 9α-Fluoro-11β-hydroxy-16β-methyl-17α-valeryloxy-21-(3-sulfopropionyloxy)-1,4-pregnadiene-3,20-dione and the sodium or potassium salts thereof.

19. 9α-Fluoro-11β,17α-dihydroxy-21-(3-sulfopropionyloxy)-4-pregnene-3,20-dione and the sodium salt thereof.

20. 17α-Butyryloxy-11β-hydroxy-21-(3-sulfopropionyloxy)-4-pregnene-3,20-dione and the sodium salt thereof.

21. 6α-Fluoro-11β,17α-dihydroxy-21-(3-sulfopropionyloxy)-1,4-pregnadiene-3,20-dione and the sodium salt thereof.

22. 11β,17aα-Dihydroxy-21-(3-sulfopropionyloxy)-D-homo-1,4-pregnadiene-3,20-dione and the sodium salt thereof.

23. 9α-Fluoro-11β,17aα-dihydroxy-21-(3-sulfopropionyloxy)-D-homo-1,4-pregnadiene-3,20-dione and the sodium salt thereof.

24. 6-Chloro-11β,17α-dihydroxy-21-(3-sulfopropionyloxy)-1,4,6-pregnatriene-3,20-dione and the sodium salt thereof.

25. 6-Chloro-11β,17α-dihydroxy-1α,2α-methylene-21-(3-sulfopropionyloxy)-4,6-pregnadiene-3,20-dione and the sodium salt thereof.

26. A pharmaceutical composition comprising an amount of a compound of claim 1 effective for treatment of shock and a pharmaceutically acceptable carrier.

27. A pharmaceutical composition comprising an amount of a salt of a corticoid 21-sulfopropionate of claim 1 effective for treatment of shock and a pharmaceutically acceptable carrier.

28. A method of treating shock which comprises administering to a patient suffering from shock an amount of a compound of claim 1 effective for treatment of shock.

* * * * *